United States Patent
Kuroki et al.

(10) Patent No.: US 11,892,436 B2
(45) Date of Patent: Feb. 6, 2024

(54) ODOR EXPLORATION METHOD AND ODOR EXPLORATION SYSTEM

(71) Applicant: AROMA BIT, INC., Tokyo (JP)

(72) Inventors: Shunichiro Kuroki, Tokyo (JP); Kenichi Hashizume, Tokyo (JP); Erika Terada, Tokyo (JP); Megumi Takahashi, Tokyo (JP); Shingo Aizawa, Tokyo (JP)

(73) Assignee: AROMA BIT, INC., Tokyo (JP)

( * ) Notice: Subject to any disclaimer, the term of this patent is extended or adjusted under 35 U.S.C. 154(b) by 186 days.

(21) Appl. No.: 17/396,958

(22) Filed: Aug. 9, 2021

(65) Prior Publication Data
US 2021/0372976 A1    Dec. 2, 2021

Related U.S. Application Data

(63) Continuation of application No. PCT/JP2019/004746, filed on Feb. 8, 2019.

(51) Int. Cl.
*G01N 33/00* (2006.01)
*G01N 29/02* (2006.01)
*G01N 29/44* (2006.01)

(52) U.S. Cl.
CPC ....... *G01N 33/0001* (2013.01); *G01N 29/022* (2013.01); *G01N 29/4454* (2013.01)

(58) Field of Classification Search
CPC ............ G01N 33/0001; G01N 29/022; G01N 29/4454; G01N 29/449; G01N 2291/0255;

(Continued)

(56) References Cited

U.S. PATENT DOCUMENTS

| 5,177,994 A | 1/1993 | Moriizumi et al. |
| 5,675,070 A | 10/1997 | Gelperin |

(Continued)

FOREIGN PATENT DOCUMENTS

| JP | 2003275289 A | 9/2003 |
| JP | 2003315298 A | 11/2003 |

(Continued)

OTHER PUBLICATIONS

Search Report for International Patent Application PCT/JP2019/004746, dated Apr. 9, 2019.

(Continued)

*Primary Examiner* — Francis C Gray
(74) *Attorney, Agent, or Firm* — FRESH IP PLC; Clifford D. Hyra; Aubrey Y. Chen

(57) ABSTRACT

The odor exploration method explores an odor based on odor information generated using a plurality of sensor elements each outputting a detection signal according to the state of adsorption by indicating an adsorption reaction unique to each odor substance, and an arithmetic unit generating the odor information by quantifying each detection signal from the sensor elements. The method includes a detection step detecting a first gas containing odor substances, a generation step generating a first odor information group generated based on a detection result of the first gas, a preparation step preparing a second odor information group generated based on a detection of a second gas, and a calculation step calculating a sum of or a difference between the second odor information group and the first odor information group based on a sum of or difference between the odor information generated for the first gas and for the second gas using the same sensor element.

12 Claims, 13 Drawing Sheets

(58) Field of Classification Search
CPC ... G01N 2291/0256; G01N 2291/0423; G01N 2291/0426; G01N 29/036; G01N 33/0034
See application file for complete search history.

(56) References Cited

U.S. PATENT DOCUMENTS

| | | | |
|---|---|---|---|
| 2002/0000115 A1* | 1/2002 | Nakano | G01N 33/0031 73/31.06 |
| 2003/0172717 A1* | 9/2003 | Kita | G01N 33/0031 73/23.34 |
| 2005/0160789 A1 | 7/2005 | Freyer | |
| 2009/0081795 A1* | 3/2009 | Furton | G01N 1/405 436/63 |
| 2010/0007460 A1* | 1/2010 | Hayashi | G06F 21/32 340/5.52 |
| 2010/0300180 A1 | 12/2010 | Bosi et al. | |
| 2020/0124577 A1* | 4/2020 | Kuroki | G01N 27/128 |

FOREIGN PATENT DOCUMENTS

| | | |
|---|---|---|
| JP | 2008308649 A | 12/2008 |
| WO | 2016031080 A1 | 3/2016 |
| WO | WO 2018/211642 A1 | 11/2018 |
| WO | WO 2018/235148 A1 | 12/2018 |

OTHER PUBLICATIONS

Supplemental Search Report for EP Application No. 19914643.2; dated Jul. 19, 2022.

S. Osowski et al.: "Differential electronic nose in on-line dynamic measurements", Metrology and Measurement Systems, vol. 21, No. 4, Jan. 1, 2014, pp. 649-662.

Notice of Reasons for Refusal, Japanese Patent Application No. 2020-570341, dated Sep. 14, 2022.

* cited by examiner

| ELAPSE TIME [SECOND] | SENSOR ELEMENT | | | | | | | | |
|---|---|---|---|---|---|---|---|---|---|
| | 11-01 | 11-02 | 11-03 | 11-04 | 11-05 | 11-06 | 11-07 | ... | 11-35 |
| 0 | 0.0 | 0.0 | 0.0 | 0.0 | 0.0 | 0.0 | 0.0 | | 0.0 |
| 1 | -1.3 | -0.3 | -2.0 | -0.3 | -5.7 | 0.7 | 0.3 | | 1.5 |
| 2 | 1.0 | 3.3 | -0.3 | 0.0 | -1.7 | -0.3 | -0.7 | | 4.5 |
| 3 | 1.0 | 0.0 | 0.3 | -0.3 | -3.3 | 0.7 | 1.3 | | 1.5 |
| 4 | 2.3 | 1.0 | -0.3 | 1.0 | -1.7 | 2.3 | 0.3 | | 0.9 |
| 5 | 4.7 | 3.7 | -1.0 | 4.7 | 0.3 | 6.3 | 3.0 | | 9.0 |
| 6 | 3.3 | 1.0 | 0.7 | 6.3 | 2.0 | 1.3 | 2.3 | | -1.9 |
| 7 | 1.7 | -1.0 | 0.0 | 1.3 | 0.7 | -1.0 | -1.0 | | 3.3 |
| 8 | 2.3 | 0.0 | 0.0 | 0.3 | -3.7 | 0.0 | -1.7 | | -0.8 |
| 9 | 1.7 | -0.3 | -1.0 | 0.7 | -6.0 | 0.3 | -1.0 | | 10.5 |
| 10 | 0.0 | -0.3 | -1.3 | 0.7 | 0.3 | -0.7 | 0.3 | | -0.3 |
| 11 | 2.0 | 1.0 | -0.3 | 1.0 | -3.0 | 0.3 | -0.7 | | 3.9 |
| 12 | 2.7 | 1.3 | 0.3 | 1.0 | -2.7 | 2.7 | 0.0 | | 5.3 |
| 13 | 3.7 | 2.3 | 0.0 | 4.7 | 0.3 | 1.3 | 3.3 | | 0.5 |
| 14 | 9.3 | 10.7 | 3.0 | 8.3 | 6.3 | 9.0 | 1.3 | | -0.3 |
| 15 | 0.0 | 5.0 | 1.7 | 2.3 | -7.7 | 4.0 | 0.0 | | 1.9 |
| 16 | -11.0 | -11.7 | -7.3 | -7.3 | -10.0 | -11.0 | -2.3 | | 2.2 |
| 17 | -13.3 | -7.7 | -4.0 | -10.0 | -8.0 | -8.3 | 1.0 | | 0.3 |
| 18 | -11.3 | 4.0 | -3.3 | -8.0 | -5.3 | -2.0 | 3.0 | | 2.4 |
| 19 | -5.7 | -3.7 | -3.7 | -0.7 | -4.0 | -2.7 | 2.7 | | 2.9 |
| 20 | 3.0 | -2.3 | -4.3 | 6.3 | -4.0 | -9.7 | 0.7 | ... | -0.5 |
| 21 | -4.7 | -5.7 | 0.0 | -5.0 | -1.3 | -6.7 | -1.7 | | 2.3 |
| 22 | 1.3 | -3.0 | -2.7 | -1.3 | -6.7 | -6.3 | -2.3 | | -3.5 |
| 23 | 0.3 | -3.3 | -1.7 | 0.0 | -4.0 | -5.3 | -2.0 | | 2.3 |
| 24 | -9.7 | -6.3 | -2.0 | -10.0 | -11.0 | -7.3 | -5.0 | | -0.9 |
| 25 | -5.3 | -8.7 | -2.7 | -9.7 | -10.7 | -7.3 | -6.0 | | 0.2 |
| 26 | -8.7 | -9.3 | -4.0 | -10.0 | -11.3 | -7.7 | -5.0 | | 3.2 |
| 27 | -7.0 | -8.7 | -2.3 | -8.3 | -10.7 | -7.7 | -5.0 | | 4.6 |
| 28 | -2.7 | -5.0 | -1.0 | -4.3 | -1.0 | -2.7 | -1.7 | | 2.4 |
| 29 | -1.3 | -4.7 | -2.3 | -4.0 | -9.7 | -4.3 | -1.7 | | 2.2 |
| 30 | -9.0 | -8.3 | -3.3 | -10.0 | -12.0 | -7.7 | -6.0 | | 1.0 |
| 31 | -8.7 | -6.0 | -1.7 | -7.3 | -6.3 | -4.3 | -4.0 | | 3.0 |
| 32 | 1.3 | -6.3 | 0.0 | 0.7 | -7.3 | -5.7 | -3.0 | | 2.4 |
| 33 | -8.7 | -8.0 | -2.7 | -10.3 | -8.0 | -5.3 | -6.7 | | 3.2 |
| 34 | -8.0 | -10.0 | -4.3 | -11.7 | -12.0 | -9.0 | -7.3 | | 2.3 |
| 35 | -5.0 | -8.3 | -3.3 | -6.7 | -12.3 | -8.0 | -6.0 | | 1.5 |
| 36 | -7.3 | -5.7 | -2.3 | -6.7 | -9.3 | -3.7 | -4.3 | | 1.6 |
| 37 | -3.7 | -6.7 | -2.0 | -4.3 | -6.3 | -5.0 | -5.0 | | 0.4 |
| 38 | -6.0 | -6.7 | -2.0 | -5.7 | -3.0 | -4.7 | -4.7 | | -1.1 |
| 39 | -5.3 | -6.0 | -2.0 | -3.7 | -8.3 | -3.7 | -3.0 | | -0.6 |
| 40 | -10.7 | -4.7 | -2.7 | -7.3 | -6.7 | -2.7 | -4.0 | | 0.8 |

Fig.2

| Odor | Sensor elements | | | | | | | | D2 |
|---|---|---|---|---|---|---|---|---|---|
| | 11-01 | 11-02 | 11-03 | 11-04 | 11-05 | 11-06 | 11-07 | ... | |
| a | 38.7 | 27.0 | 12.7 | 27.0 | 28.0 | 27.0 | 10.7 | ... | |
| b | 7.6 | 24.1 | 38.6 | 28.2 | 15.8 | 3.4 | 12.3 | | |
| ... | | | | | | | | | |

| Examples | First odor information group | Second odor information group | Type of odor information | Calculation | Adjustment | Type of Degree of Similarity | Odor image |
|---|---|---|---|---|---|---|---|
| 1-1 | Lemon +Cinnamon | Lime | Difference value | Sum | — | Cosine similarity | |
| 1-2 | Lemon +Cinnamon | Lime | Slope | Sum | — | Cosine similarity | |
| 1-3 | Lemon +Cinnamon | Lime | Slope | Sum | — | Pearson correlation coefficient | |
| 1-4 | Lemon +Lime +Cinnamon | Lime +Cinnamon | Difference value | Difference | Delete odor information equal to or smaller than 0 | Cosine similarity | |
| 1-5 | Lemon +Lime +Cinnamon | Lime +Cinnamon | Difference value | Difference | Delete odor information equal to or smaller than 0 | Pearson correlation coefficient | |
| 1-6 | Lemon +Lime +Cinnamon | Lime +Cinnamon | Logarithmic value of difference value | Difference | Delete odor information equal to or smaller than 0 | Cosine similarity | |
| 1-7 | Lemon +Lime +Cinnamon | Lemon +Cinnamon | Logarithmic value of difference value | Difference | Delete odor information equal to or smaller than 0 | Inter-vector distance | |
| 1-8 | Cola (Cola drink A) | Lime +Cinnamon | Index | Difference | Delete odor information equal to or smaller than 0 | Cosine similarity | |
| 1-9 | Cola (Cola drink A) | Lemon +Lime | Index | Difference | Delete odor information equal to or smaller than 0 | Inter-vector distance | |
| 1-10 | Cola (Cola drink A) | Lemon +Cinnamon | Index | Difference | Delete odor information equal to or smaller than 0 | Deviation pattern similarity | |

| Examples | Degree of similarity | | |
|---|---|---|---|
| | First place | Second place | Third place |
| 1-1 | Cola drink A | Black tea A | Aroma oil D |
| Score value | 0.9375 | 0.937 | 0.9346 |
| Cosine similarity | 0.9808 | 0.9805 | 0.979 |
| Inter-vector distance | 68.0132 | 71.1948 | 73.4982 |
| Pearson correlation coefficient | 0.8236 | 0.8405 | 0.7652 |
| Deviation pattern similarity | -0.9017 | -0.9242 | -0.9307 |
| 1-2 | Cola drink B | Coffee drink A | Coffee drink B |
| Score value | 0.9352 | 0.9324 | 0.9307 |
| Cosine similarity | 0.9793 | 0.9775 | 0.9764 |
| Inter-vector distance | 43.1803 | 47.4109 | 43.9714 |
| Pearson correlation coefficient | 0.8273 | 0.7784 | 0.7676 |
| Deviation pattern similarity | -0.8105 | -0.8889 | -0.8117 |
| 1-3 | Cola drink B | Framboise | Coffee drink A |
| Score value | 0.9352 | 0.926 | 0.9324 |
| Cosine similarity | 0.9793 | 0.9731 | 0.9775 |
| Inter-vector distance | 43.1803 | 44.9267 | 47.4109 |
| Pearson correlation coefficient | 0.8273 | 0.7841 | 0.7784 |
| Deviation pattern similarity | -0.8105 | -0.8142 | -0.8889 |
| 1-4 | Shower gel | Essentail oil A | Aroma oil C |
| Score value | 0.8759 | 0.8696 | 0.8675 |
| Cosine similarity | 0.925 | 0.9173 | 0.9146 |
| Inter-vector distance | 99.0841 | 93.1755 | 57.578 |
| Pearson correlation coefficient | 0.7466 | 0.7288 | 0.6941 |
| Deviation pattern similarity | 0.9965 | 0.9957 | 0.9904 |
| 1-5 | Shower gel | Essentail oil A | Alcohol drink A |
| Score value | 0.8759 | 0.8696 | 0.847 |
| Cosine similarity | 0.925 | 0.9173 | 0.8867 |
| Inter-vector distance | 99.0841 | 93.1755 | 198.5911 |
| Pearson correlation coefficient | 0.7466 | 0.7288 | 0.7081 |
| Deviation pattern similarity | 0.9965 | 0.9957 | 0.9984 |
| 1-6 | Lemon drink A | Alcohol drink B | Alcohol drink C |
| Score value | 0.8426 | 0.8376 | 0.8313 |
| Cosine similarity | 0.8803 | 0.8727 | 0.8628 |
| Inter-vector distance | 10.2608 | 10.3595 | 11.0863 |
| Pearson correlation coefficient | 0.6956 | 0.7042 | 0.7027 |
| Deviation pattern similarity | 0.782 | 0.8475 | 0.8433 |
| 1-7 | Lemon drink A | Alcohol drink B | Reagent D |
| Score value | 0.8426 | 0.8376 | 0.8308 |
| Cosine similarity | 0.8803 | 0.8727 | 0.8621 |
| Inter-vector distance | 10.2608 | 10.3595 | 10.6048 |
| Pearson correlation coefficient | 0.6956 | 0.7042 | 0.5656 |
| Deviation pattern similarity | 0.782 | 0.8475 | 0.8956 |
| 1-8 | Fragrance A | Black tea B | Alcohol drink D |
| Score value | 0.8645 | 0.8598 | 0.8593 |
| Cosine similarity | 0.9107 | 0.9045 | 0.9039 |
| Inter-vector distance | 11.2962 | 10.9251 | 10.4902 |
| Pearson correlation coefficient | 0.7245 | 0.708 | 0.7052 |
| Deviation pattern similarity | -0.2946 | -0.2556 | 0.0241 |
| 1-9 | Synthetic sample B | Alcohol drink E | Black tea C |
| Score value | 0.8806 | 0.8633 | 0.8692 |
| Cosine similarity | 0.9305 | 0.9091 | 0.9167 |
| Inter-vector distance | 4.9201 | 5.086 | 5.1082 |
| Pearson correlation coefficient | 0.7629 | 0.6805 | 0.7169 |
| Deviation pattern similarity | 0.765 | 0.7857 | 0.7558 |
| 1-10 | Aroma oil A | Aroma oil B | Shampoo A |
| Score value | 0.6613 | 0.661 | 0.6679 |
| Cosine similarity | 0.4854 | 0.4845 | 0.5033 |
| Inter-vector distance | 63.8551 | 64.1381 | 63.7977 |
| Pearson correlation coefficient | -0.313 | -0.22 | -0.3016 |
| Deviation pattern similarity | -0.2054 | -0.228 | -0.2377 |

| Examples | First odor information group | Second odor information group | Type of odor information | Calculation | Adjustment | Type of Degree of Similarity | Odor image |
|---|---|---|---|---|---|---|---|
| 2-1 | Isovaleric acid | Vanillin | Difference value | Sum | — | Cosine similarity | |
| 3-1 | Tobacco +Geraniol +Benzaldehyde +Perillaldehyde | Geraniol +Benzaldehyde +Perillaldehyde | Logarithmic value of difference value | Difference | Delete odor information equal to or smaller than 0 | Pearson correlation coefficient | |
| 3-2 | Tobacco +Geraniol +Benzaldehyde +Perillaldehyde | Geraniol +Benzaldehyde +Perillaldehyde | Difference value | Difference | Delete odor information equal to or smaller than 0 | Inter-vector distance | |
| 3-3 | Apple juice +Chelate Lemon | Lemon oil | Logarithmic value of slope | Difference | Delete odor information equal to or smaller than 0 | Cosine similarity | |

FIG. 12

1300

| Examples | Degree of similarity | | | | | |
|---|---|---|---|---|---|---|
| | First place | | Second place | | Third place | |
| 2-1 | Body milk A | | Coffee drink D | | Chocolate A | |
| Score value | 0.9377 | | 0.9368 | | 0.9340 | |
| Cosine similarity | 0.9809 | | 0.9803 | | 0.9786 | |
| Inter-vector distance | 86.9743 | | 83.7274 | | 77.8738 | |
| Pearson correlation coefficient | 0.8820 | | 0.8564 | | 0.8606 | |
| Deviation pattern similarity | -0.9578 | | -0.9470 | | -0.9141 | |
| 3-1 | Smoker's breath A | | Reagent B | | Bedbug | |
| Score value | 0.8168 | | 0.8225 | | 0.8099 | |
| Cosine similarity | 0.8390 | | 0.8485 | | 0.8269 | |
| Inter-vector distance | 86.9678 | | 85.3490 | | 83.7987 | |
| Pearson correlation coefficient | 0.4881 | | 0.4740 | | 0.4733 | |
| Deviation pattern similarity | -0.6182 | | -0.6068 | | -0.4991 | |
| 3-2 | Smoker's breath A | | Machine oil | | Hair dressing A | |
| Score value | 0.8270 | | 0.8244 | | 0.8243 | |
| Cosine similarity | 0.8558 | | 0.8517 | | 0.8514 | |
| Inter-vector distance | 53.3292 | | 54.2883 | | 55.9742 | |
| Pearson correlation coefficient | 0.5181 | | 0.4831 | | 0.4838 | |
| Deviation pattern similarity | 0.8931 | | 0.7661 | | 0.7447 | |
| 3-3 | Fruit juice drink A | | Reagent E | | Coffee drink C | |
| Score value | 0.4847 | | 0.4733 | | 0.4717 | |
| Cosine similarity | -0.0482 | | -0.0839 | | -0.0888 | |
| Inter-vector distance | 39.4661 | | 38.7884 | | 39.2400 | |
| Pearson correlation coefficient | 0.6615 | | 0.5304 | | 0.6120 | |
| Deviation pattern similarity | 0.7552 | | 0.7123 | | 0.7369 | |

FIG. 13

ODOR EXPLORATION METHOD AND ODOR EXPLORATION SYSTEM

CROSS-REFERENCE TO RELATED APPLICATION

The present application is a continuation application of International Application No. PCT/JP2019/004746, filed Feb. 8, 2019. The contents of this application are incorporated herein by reference in its entirety.

BACKGROUND

Field

The present invention relates to an odor exploration method and an odor exploration system including exploring odors based on odor information.

Description of the Related Art

In order to measure an odor of an atmosphere, a sensor including a quartz oscillator that specifically adsorbs an odor substance in the atmosphere is known (refer to Patent Document 1: JP 5-187986 A).

By using such a sensor, the odor of an atmosphere can be detected, and the detected signals are converted into numerical values to obtain an odor information of the respective atmospheres. However, it is difficult to determine what kind of odor is obtained when a specific odor and other odor are mixed. In addition, it is difficult to determine what kind of odor should be mixed with a specific odor in order to obtain a target odor.

The present invention has been made in view of the above-mentioned circumstances, and it is an exemplary problem of the present invention to provide an odor exploration method and an odor exploration system which are able to explore an odor obtained when different odors are mixed with each other or an odor mixed with a particular odor in order to obtain a desired odor is mixed with each other.

SUMMARY

In order to attain the object described above, the present invention is configured as follows.

[1] An odor exploration method exploring odor based on odor information generated by
 (1) a plurality of sensor elements each outputting a detection signal according to the state of adsorption by indicating an adsorption reaction unique to each odor substance, and
 (2) an arithmetic unit generating the odor information which consists of numerical values, by quantifying each detection signal outputted from the plurality of sensor elements;
wherein the odor exploration method comprises:
a detection step detecting a first gas containing a plurality of odor substances with the plurality of sensor elements;
a generation step generating a first odor information group consisting of the odor information generated based on a detection result of the first gas;
a preparation step preparing a second odor information group consisting of odor information generated based on a detection of a second gas different from the first gas with the plurality of sensor elements; and
a calculation step calculating a sum of or a difference between the second odor information group and the first odor information group based on a sum of or difference between the odor information generated for the first gas and for the second gas using the same sensor element.

[2] An odor exploration system comprising:
an odor sensor having a plurality of sensor elements each outputting a detection signal according to the state of adsorption by indicating an adsorption reaction unique to each odor substance, and detecting a first gas containing a plurality of odor substances with the plurality of sensor elements;
a generator generating odor information which consists of numerical values by quantifying each detection signal from the plurality of sensor elements, and generating a first odor information group consisting of the odor information generated based on a detection result of the first gas;
a preparer preparing a second odor information group consisting of odor information generated based on a detection of a second gas different from the first gas with the plurality of sensor elements; and
a calculator calculating a sum of or a difference between the second odor information group and the first odor information group based on a sum of or difference between the odor information generated for the first gas and for the second gas using the same sensor element.

Further objects or other characteristics of the present invention will be apparent by preferred embodiments described below with reference to the attached drawings.

According to the present invention, it is possible to provide an odor exploration method and an odor exploration system which are able to explore an odor obtained when different odors are mixed with each other or an odor mixed with a particular odor in order to obtain a desired odor is mixed with each other.

BRIEF DESCRIPTION OF THE DRAWINGS

FIG. 2 is a detection signal database D1 detected in the detection step S1;

FIG. 6 shows an exemplary odor information database D2;

FIG. 10 shows the various requirements of Examples 1-1 to 1-10;

FIG. 11 shows the selection results of Examples 1-1 to 1-10;

FIG. 12 shows the various requirements of Examples 2-1 and 3-1 to 3-3; and

FIG. 13 shows the selection results of Examples 2-1 and 3-1 to 3-3.

DETAILED DESCRIPTION

Embodiment 1

Figure 1:
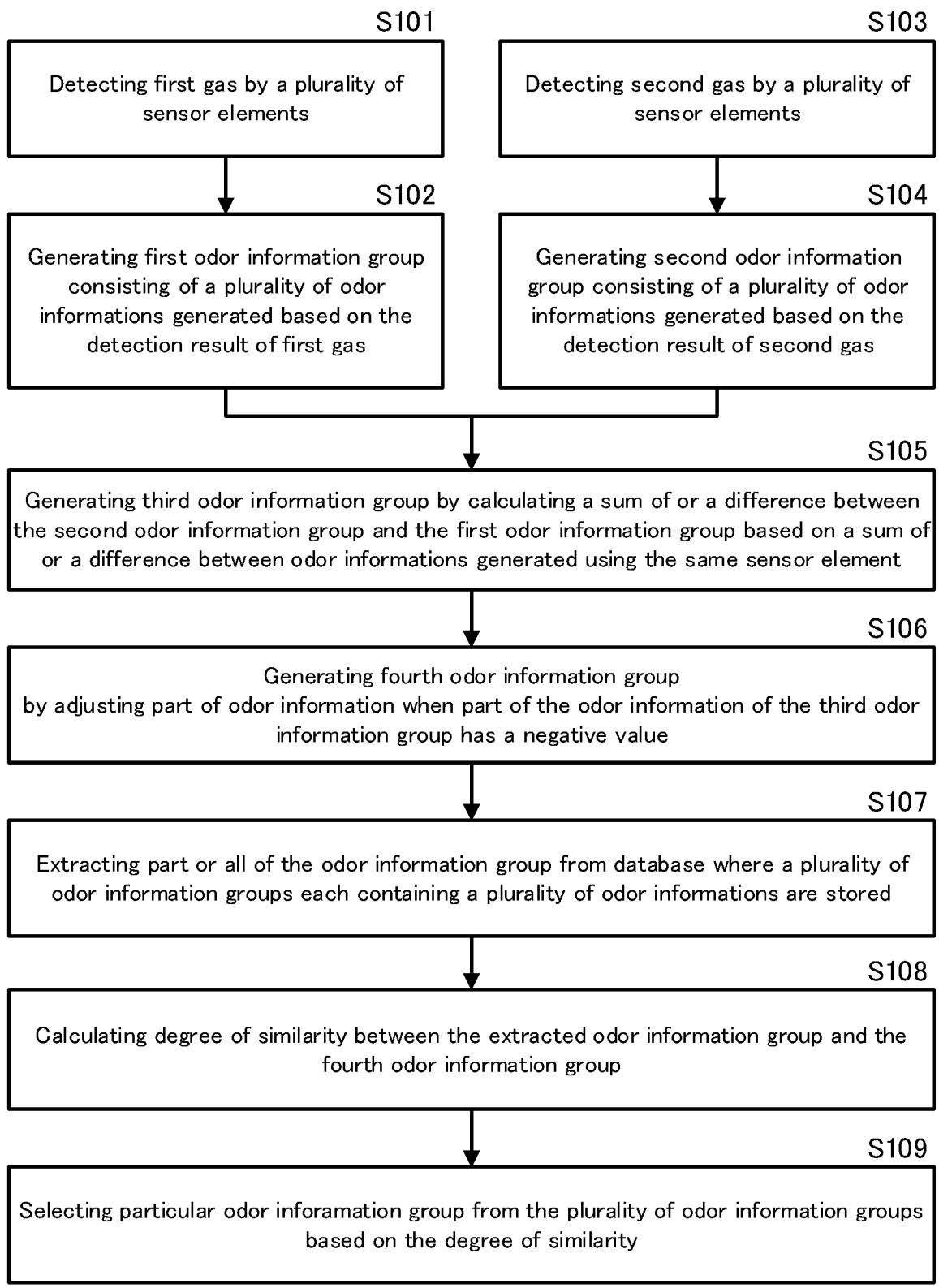
FIG. 1 is a flow chart showing the steps of odor exploration method according to Embodiment 1.

Hereinafter, respective steps of an odor exploration method according to Embodiment 1 will be described in order by referring to FIG. 1. FIG. 1 is a flow chart showing the steps of odor exploration method according to Embodiment 1.

In Embodiment 1, the "odor" can be acquired by a human or living things including the human as olfactory information and corresponds to a concept including a molecular simple substance or a group of molecules made of different molecules gathered with respective concentrations.

In Embodiment 1, the molecular simple substance or the group of molecules made of different molecules gathered with respective concentrations included in the odor is referred to as an "odor substance". However, in a broad sense, the odor substance may broadly mean a substance which can be adsorbed on a substance adsorbing membrane of an odor sensor, which will be described below. That is, since the "odor" contains a plurality of odor substances responsible for the odor in many cases, and a substance not recognized as the odor substance or an unknown odor substance may be present, a substance generally not regarded as an odor causing substance may be contained.

In the odor exploration method according to Embodiment 1, the respective steps of a detection step S1, a generation step S2, a preparation step S3, and a calculation step S4 are performed based on odor information generated using a plurality of sensor elements, and an arithmetic unit. The odor exploration method according to Embodiment 1 may further include adjustment step S5, extraction step S6, similarity calculation step S7, and selection step. Each step will be described below.

<Detection Step S1>

In the detection step S1, a first gas is detected by a plurality of sensor elements 11 (see FIG. 7) (S101 of FIG. 1). The first gas, like any other gas, is a gas containing a plurality of odor substances. In the detection step S1, in addition to the first gas, other gases may be detected, such as, for example, a second gas (S103 of FIG. 1). The first gas and the other gases are not detected simultaneously, but are detected individually.

The sensor element 11 is an element constituting an odor sensor 10 (refer to FIG. 7), and outputs a detection signal according to its state of adsorption by indicating an adsorption reaction unique to each odor substance. That is, the sensor element 11 shows a unique adsorption reaction for each of the many kinds of odor substances contained in the first gas. By detecting the first gas using a plurality of sensor elements indicating unique adsorption reactions to the first gas, unique detection signals can be outputted from each of the plurality of sensor elements 11. Of course, when different odor substance gases are detected, different detection signals are outputted from each of the plurality of sensor elements 11 than when the first gas was detected. The specific configuration of the sensor element 11 will be described later.

FIG. 2 is a detection signal database D1 detected in the detection step S1. In the detection signal database D1, the sensor element 11s and the detection signal detected in each of sensor elements 11 are shown in association with the respective other. In the detection signal database D1 shown in FIG. 2, the respective detection signals are stored in a manner associated with a total of 35 sensor elements 11 from sensor elements 11-01 to 11-35. Incidentally, in FIG. 2, for the convenience of the description, the description of the sensor elements 11-08 to 11-34 is omitted.

Detection signal is specifically raw data detected by the respective sensor elements 11. In a case where the odor sensor 10, for example, is a quartz oscillator sensor (QCM), a temporal change in a resonance frequency of a quartz oscillator can be the raw data that is generated by the sensor element 11. That is, a detection signal from the sensor element 11 may be a resonance frequency at a plurality of time points having different elapse times from an operation start of the odor sensor 10. For example, as shown in FIG. 2, the detection signal detected in the sensor element 11-01 has a resonant frequency of "9.3" detected at 14 seconds and a resonant frequency of "−11.0" detected at 16 seconds, when the resonant frequency at 0 seconds after operation start of the odor sensor 10. Further, the detection signal detected in the sensor element 11-02 has a resonance frequency of "10.7" detected at 14 seconds after operation start of the odor sensor 10 and a resonance frequency of "−11.7" detected at 16 seconds, when the resonance frequency at 0 seconds after operation start of odor sensor 10. The time interval for recording detection signal is not particularly limited, but may be, for example, a time interval of 1 second.

The detection by the sensor element 11 is preferably performed a plurality of times, and an average value of the raw data of the detection performed a plurality of times is preferably used as detection signal. The number of times of detection is not particularly limited, and for example, can be three times. An average value according to an arithmetic average (an arithmetic means) can be adopted as the average value.

<Generation Step S2>

In the generation step S2, a first odor information group is generated based on the detection signal of the first gas detected in detection step S1 (S102 to FIG. 1). From the detection signal of the first gas, an odor information is generated by an arithmetic unit. That is, the detection signal outputted from each sensor elements by detecting the first gas is quantified to numerical values by the arithmetic unit, and odor information corresponding to the respective sensor element is generated. From a detection signal outputted by a predetermined sensor element, odor information corresponding one-to-one to a predetermined sensor element is generated by an arithmetic unit. A specific configuration of the arithmetic unit will be described later.

Odor information consists of numerical values obtained by quantifying a detection signal outputted by a sensor element by an arithmetic unit. In other words, odor information consists of numerical values obtained by quantifying the odor detected by the respective sensor elements. When the first gas is detected using n sensor elements, n odor information values are obtained. The n odor information values obtained by detecting the first gas are collectively referred to as a first odor information group. The quantification by the arithmetic unit is preferably a quantification such that the numerical value is 0 (zero) or a positive value, and the odor information is preferably 0 (zero) or a positive value. An odor can be evaluated more accurately when the odor information has a value of 0 (zero) or positive values instead of negative value. It is also advantageous to determine or compare a sum of or a difference of odor information when the odor information has a value of 0 (zero) or positive value.

The generation step S2 can be executed by, for example, sub-steps of a difference value calculation sub-step S2-1, a logarithmic arithmetic sub-step S2-2, a value classifying sub-step S2-3, and an index generating sub-step S2-4.

Difference Value Calculation Sub-Step S2-1>

In the difference value calculation sub-step S2-1, for each of the detection signals detected in the detection step S1, the difference (difference value) between the maximal value and the first minimal value after passing through the maximal value (hereinafter also referred to as "minimal value immediately after the maximal value") is calculated. Then, in a case where there are a plurality of difference values (between the maximal value and the minimal value immediately after the maximal value), the difference value having the largest value is adopted as the difference value of the measurement result. In this manner, for each measurement result, a difference value associated with each of the plurality of sensor element 11 is obtained. Further, by dividing the difference value by the time until it changes from the maximal value to the minimal value immediately after the maximal value, it is possible to obtain the slope for the respective detection signal.

Figure 3:
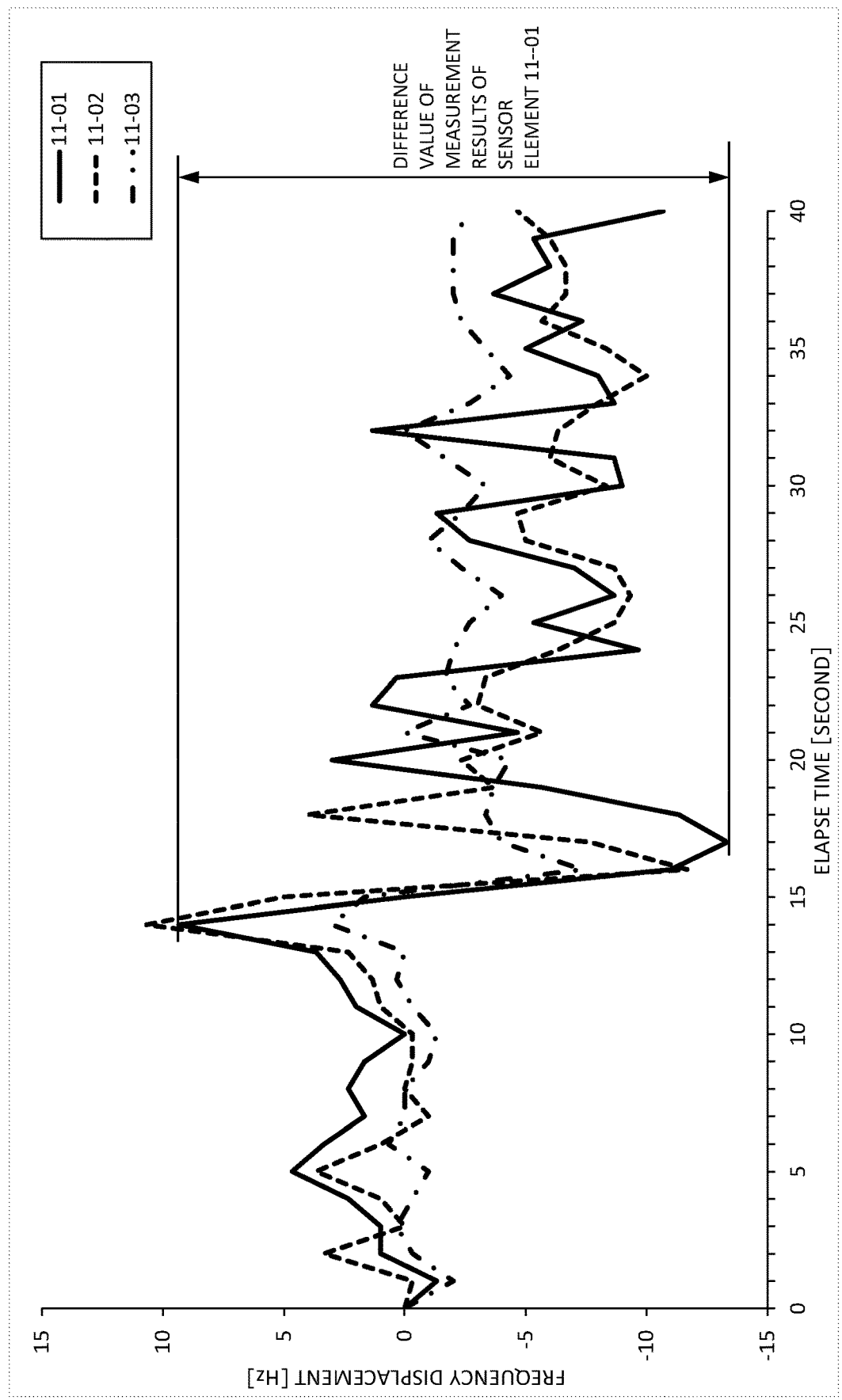
FIG. 3 is a graph showing a detection signal detected in detection step S1.

FIG. 3 is a graph showing a detection signal detected in detection step S1. In FIG. 3, the vertical axis denotes a displacement amount [Hz] of a resonance frequency which is detected after a predetermined time, on the basis of the resonance frequency after 0 seconds from the operation start of the odor sensor 10, and the horizontal axis denotes an elapse time [second] from the operation start of the odor sensor 10. In FIG. 3, among detection signal shown in detection signal database D1, detection signal for sensor element 11-01, 11-02, 11-03 is shown. In FIG. 3, sensor element 11-01 shows detection signal as a solid line, sensor element 11-02 shows detection signal as a broken line, and sensor element 11-03 shows the as a dashed-dotted line. It is obvious that graphs can also be prepared with respect to other sensor elements 11-04 to 11-35, similarly. In FIG. 3, for sensor element 11-01, the difference value of the detection signals is "22.6 Hz". That is, in the detection signals for the sensor element 11-01, the difference value between the maximal value "9.3 Hz" at elapse time 14 seconds after the start of operation of the odor sensor 10 and the minimal value "−13.3 Hz" at elapse time 17 seconds after the start of operation of the odor sensor 10.

In the calculation of the difference values, the scope of elapse time after operation of the odor sensor 10 is started may be limited. For example, in a case where the measurement of the odor of the sample is started after 15 seconds from the operation start of the odor sensor 10, and the measurement of the odor of the sample is ended after 20 seconds from the operation start of the odor sensor 10, the range of the elapse time for calculating the difference value can be set to an elapse time of 14 seconds to 25 seconds from the operation start of the odor sensor 10. Incidentally, the range of the elapse time can be arbitrarily set.

<Logarithmic Arithmetic Sub-Step S2-2>

In the logarithmic arithmetic sub-step S2-2, a logarithmic arithmetic operation is performed with respect to each of the difference values calculated in the difference value calculation sub-step S2-1, and thus, a logarithmic value associated with each of the plurality of sensor elements 11 is obtained. In the logarithmic arithmetic operation, the base is not particularly limited, and for example, can be 2. Incidentally, the difference value is a difference between the maximal value and the minimal value and is a positive value (real number). In the same manner as the difference values, the logarithmic value can be obtained for the slope.

<Value Classifying Sub-Step S2-3>

In the value classifying sub-step S2-3, each of the logarithmic values obtained in the logarithmic arithmetic sub-step S2-2 is classified into ranges in accordance with the magnitude of the value. The number of classified ranges is not particularly limited, and can be three ranges to five ranges, and the like, for example. Hereinafter, a case where the value is classified into three ranges will be described.

In the value classifying sub-step S2-3, first, among the plurality of logarithmic values of the respective samples which are obtained in the logarithmic arithmetic sub-step S2-2, a maximum logarithmic value and a minimum logarithmic value are identified. Next, a quotient in a case where a difference between the maximum logarithmic value and the minimum logarithmic value is divided by 3 is calculated. A numerical range between the maximum logarithmic value and the minimum logarithmic value can be partitioned into trisected ranges by using the quotient obtained as described above. That is, the numerical range can be trisected into a range from the minimum logarithmic value to a value in which the quotient is added to the minimum logarithmic value, a range from the value in which the quotient is added to the minimum logarithmic value to a value in which twice the quotient is added to the minimum logarithmic value, and a range from the value in which twice the quotient is added to the minimum logarithmic value to the maximum logarithmic value.

Next, each of the logarithmic values associated with each of the sensor elements 11 is classified into any range of three ranges. To each of the logarithmic values, a flag for identifying the classified range may be provided. For example, for the three trisected ranges, flags such as (1), (2), and (3) in an increasing order can be provided. Accordingly, the detection signal associated with each of the sensor elements 11 can be classified into three stages in accordance with the magnitude of the value.

Figure 4:
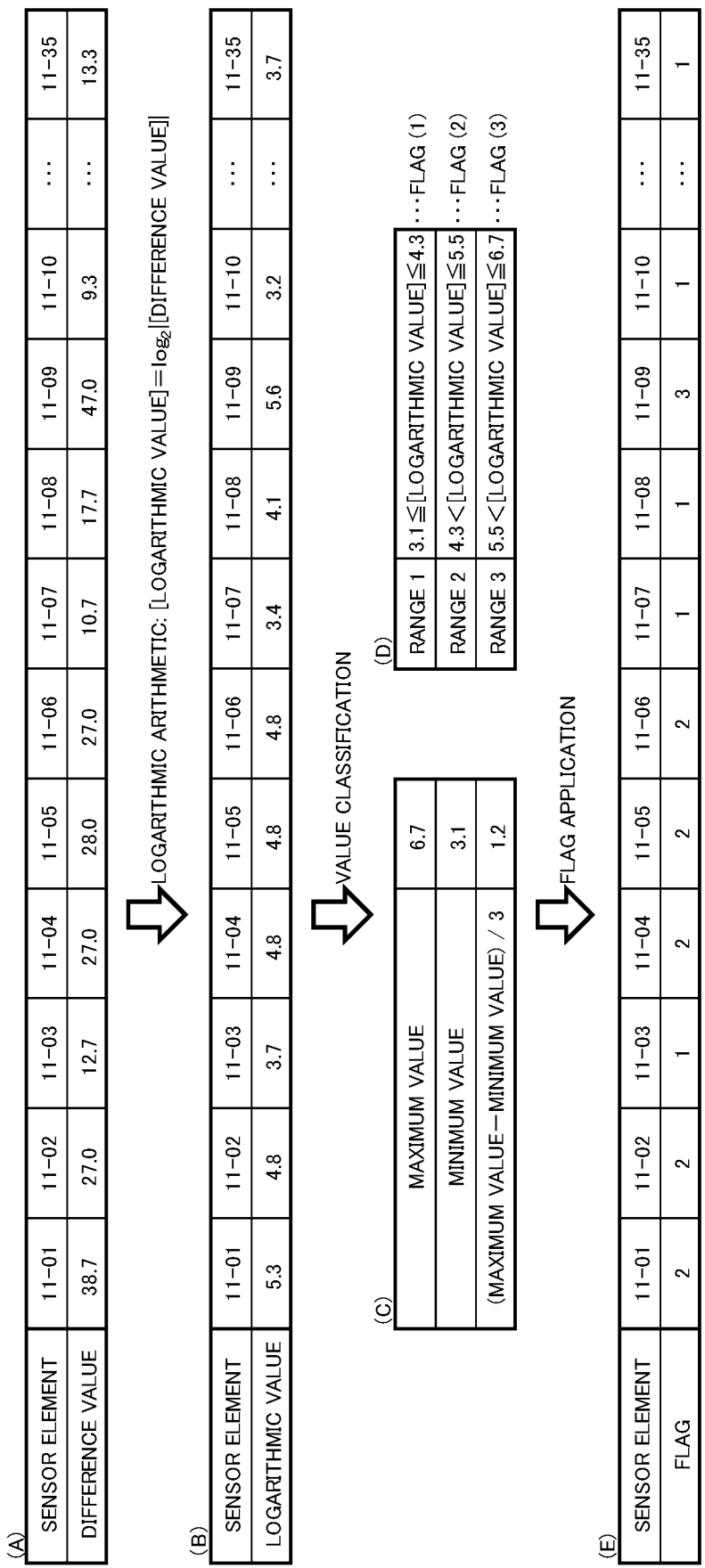
FIG. 4 is a diagram illustrating an outline of the generation step S2 of Embodiment 1.

The generation step S2 described above will be described in more detail by using FIG. 4. FIG. 4 is a diagram illustrating an outline of the generation step S2 of Embodiment 1. In FIG. 4, Table (A) is a table showing the difference values calculated in difference value calculation sub-step S2-1 for certain samples. The value of each of the difference values of each of the sensor elements 11-01 to 11-35 is shown. For example, in Table (A), the difference value obtained in sensor element 11-01 is "38.7", and the difference value obtained in sensor element 11-02 is "27.0". Incidentally, for the convenience of the description, indication of the values of the sensor elements 11-11 to 11-34 will be omitted (the same applies to Table (B) and Table (E) described below).

Next, according to the logarithmic arithmetic sub-step S2-2, the difference values of each of the sensor elements 11 are subjected to logarithmic arithmetic processing. Here, the logarithmic arithmetic operation is represented by Formula (1) described below. That is, an absolute value of the value of the difference value is subjected to logarithmic arithmetic operation by setting the base to 2, and thus, the logarithmic value is obtained.

$$[\text{Logarithmic value}] = \log 2 |[\text{difference value}]| \quad \text{Formula (1)}$$

Table (B) is a table showing the logarithmic values of each of the sensor elements 11 which are obtained in the logarithmic arithmetic sub-step S2-2. For example, in Table (B), the logarithmic value calculated based on the difference value obtained in sensor element 11-01 is "5.3", the logarithmic value calculated based on the difference value obtained in sensor element 11-02 is "4.8".

Next, according to the value classifying sub-step S2-3, the logarithmic values of each of the sensor elements 11 are classified into three ranges on the basis of the obtained logarithmic value. Specifically, first, in the sample being measured, in the logarithmic values of the respective sensor elements 11, the maximum logarithmic value (maximum value) and the minimum logarithmic value (minimum value) are identified. Then, a quotient in a case where the difference between the maximum value and the minimum value is divided by 3 is calculated. The identified maximum value and minimum value, and the calculated quotient are shown in Table (C). In Table (C), the identified maximum value is "6.7", the identified minimum value is "3.1", and the calculated quotient is "1.2".

The logarithmic values of each of the sensor elements 11 are classified into three levels on the basis of the identified maximum value and minimum value, and the calculated quotient. The classification is performed on the basis of a classification rule as shown in Table (D). Specifically, the classification is performed on the basis of a classification rule in which a range of the smallest logarithmic values (range 1) is a range of $3.1 \leq [\text{Logarithmic Value}] \leq 4.3$, a range of the second smallest logarithmic values (range 2) is a range of $4.3 \leq [\text{Logarithmic Value}] \leq 5.5$, and a range of the largest logarithmic values (range 3) is a range of $5.5 \leq [\text{Logarithmic Value}] \leq 6.7$.

Next, flags are applied to each of the sensor elements 11 on the basis of the classification result. The result of applying the flag to each of the sensor elements 11 is shown in Table (E). Flags (1) are applied to the sensor elements 11 in which the logarithmic value corresponding to range 1 is obtained, flags (2) are applied to the sensor elements 11 in which the logarithmic value corresponding to range 2 is obtained, and flags (3) are applied to the sensor elements 11 in which the logarithmic value corresponding to range 3 is obtained. For example, in Table (E), a flag (2) is applied to the sensor element 11-01, a flag (1) is applied to the sensor element 11-03, and a flag (3) is applied to the sensor element 11-09.

<Index Generating Sub-Step S2-4>

In the index generating sub-step S2-4, a logarithmic value (measured result) classified in the value classifying sub-step S2-3, based on the logarithmic value (detected result) corresponding to each sensor element 11, an index is generated. The index has a value corresponding to the respective sensor element 11.

Figure 5:
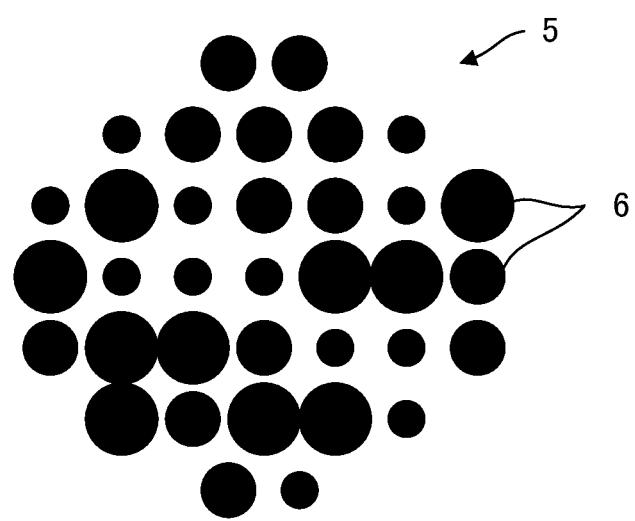
FIG. 5 is an example of an image represented based on the indices generated in generation step S2 of Embodiment 1.

The index is a data which provide the basis of image data for representing the odor of the samples in an odor image 5 (refer to FIG. 5). The index is a data indicating the position or the size, the color, the shape, and the like of small images 6, but not a data (pixel data) indicating information of the color, the position, and the like of each pixel forming the odor image 5. The odor image 5 prepared on the basis of the indices includes a plurality of small images 6 represented by indices corresponding to each of the sensor elements 11. The odor image 5 can be represented in the predetermined display mode, as an assembly of the plurality of small images 6. Each of the small images 6 can be varied in accordance with the magnitude of the values of the corresponding indices. Specifically, the size, the color, and the shape of the small images 6 can be varied in accordance with the magnitude of the values of the corresponding indices. That is, in the index generating sub-step S2-4, the index is generated such that the odor of the sample is represented in the odor image 5 in the predetermined display mode. In the index generating sub-step S2-4, the indices are generated so that each of the small images 6 changes according to the magnitude of values of the indices.

FIG. 5 is an example of an image represented based on the indices generated in generation step S2 of Embodiment 1. The odor image 5 illustrated in FIG. 5 includes 35 small images 6, and each of the small images 6 is in the shape of a circle. Each of the small images 6 corresponds to each of the sensor elements 11-01 to 11-35, and is aligned in order from the upper left side. Specifically, in FIG. 5, two small images 6 in the first row from the upper side respectively correspond to the sensor elements 11-01 and 11-02 in order from the left side, and five small images 6 in the second row from the upper side respectively correspond to the sensor elements 11-03 to 11-07 in order from the left side. In addition, the small image 6 corresponding to the sensor element 11-03 (flag (1)) is represented by a small circle, the small image 6 corresponding to the sensor element 11-09 (flag (3)) is represented by a large circle, and the small image 6 corresponding to the sensor element 11-01 (flag (2)) is represented by a circle having a size between the small circle and the large circle.

In FIG. 5, the shape of all of the small images 6 is represented by a circle, but the shape of each of the small images 6 is not limited to a circle, and may be a square, a rectangle, a rhomboid, other indefinite shapes, and the like. In addition, it is not necessary that the shapes of all of the small images 6 are coincident with each other, and the small images 6 may respectively have different shapes. In FIG. 5, the color of each of the small images 6 is represented in black, but the color of each of the small images 6 is not limited to black, and may be represented by an arbitrary color. In addition, it is not necessary that the colors of all of the small images 6 are coincident with each other, and the small images 6 may be respectively represented by different colors.

In FIG. 5, each of the small images 6 is represented such that the size is different in accordance with the magnitude of the value of the corresponding index. Specifically, the small image 6 is displayed large when the value of the index increases, and the small image 6 is displayed small when the value of the index decreases. Here, the size of each of the small images 6 to be displayed may be classified into a plurality of levels in accordance with the level classified in the value classifying sub-step S2-3. That is, in the value classifying sub-step S2-3, in a case where the classification is performed into three levels of flags (1), (2), and (3), the size of the small image 6 can also be classified and displayed in three levels.

In the predetermined display mode, it is preferable that an interval between the small images 6 is constant (an equal interval). In addition, in the predetermined display mode, it is preferable that the position of each of the small images 6 (the center or the gravity center of each of the small images 6) is constant (not changed in accordance with the value of the index). As described above, the position or the interval of each of the small images 6 is constant, and thus, in a case where the size or the shape of each of the small images 6 is changed in accordance with the size of the value of the index, it is possible to easily visually grasp the changed small image 6 by comparing the odor images 5 before and after being changed with each other. Incidentally, the interval between the small images 6 is not limited to being constant (the equal interval), and the odor image 5 may be a combination of a plurality of small images 6 having different shapes.

Preparation Step S3

In the preparation step S3, a second gas is detected by a sensor element and quantified into numerical value by an arithmetic unit to generate a second odor information group, similarly to the first gas (S104 of FIG. 1).

Calculation Step S4

In the calculation step S4, a sum of or a difference between the first odor information group and the second odor information group is calculated and a third odor information group as a result is generated (S105 in FIG. 1). The sum of or the difference between the first odor information group and the second odor information group is calculated based on the sum of or the difference between the odor information generated for the first gas and for the second gas using the same sensor element.

When the sum of the odor information for the first gas and for the second gas is obtained, one odor information numerical value as it is may be added to the other odor information numerical value. Alternatively, one odor information numerical value may be multiplied by an arbitrary coefficient and then added to the other odor information numerical value, or both odor information numerical values may be multiplied by an arbitrary coefficient and then added together. When the difference between the odor information generated for the first gas and for the second gas is obtained, one odor information numerical value as it is may be subtracted from the other odor information numerical value. Alternatively, one odor information numerical value may be multiplied by an arbitrary coefficient and then subtracted from the other odor information numerical value, or both odor information numerical values may be multiplied by an arbitrary coefficient and then subtracted from the other. Although there is no particular limitation on the coefficient for multiplying odor information numerical values, an odor coefficient can be determined by considering the difference in the detection intensity between the odors due to the difference in the adsorption amount of odor substance to the substance adsorbing membrane or the like.

As used herein, "using the same sensor element" may refer to a single sensor element for detection of both the first gas and the second gas, or separate sensor elements with the same configuration for detection of the first gas and the second gas, respectively. It is assumed that the same detection signal can be obtained when a sensor element having the same configuration is used to detect gases under a fixed condition.

The plurality of sensor element for detecting the first gas and the plurality of sensor element for detecting the second gas may be all of the same sensor element, or may be partially different sensor elements. It is preferable that a plurality of sensor elements for detecting the first gas and a plurality of sensor elements for detecting the second gas are all of the same sensor element. The more identical sensor element used for detection, the more numerical values are obtained, and thus the resulting odor can be more accurately represented.

<Adjustment Step S5>

In calculation step S4, some of the odor information included in the third odor information group as a result of difference between the second odor information group and the first odor information group may be a negative value. Since odor information preferably consists of positive numerical values, if some odor information numerical values are negative, a fourth odor information group can be generated by adjusting some odor information (S106 in FIG. 1).

For example, the following adjustment steps S5-A to S5-D can be used as adjustment step S5 for adjusting odor information that has a negative value in the third odor information group. The adjustment step S5 is not limited to these adjustment steps S5-A to S5-D, and odor information having a negative value can be adjusted by other methods.

(Adjustment Step S5-A)

The adjustment step S5-A is a step excluding particular odor information from the third odor information group when the particular odor information contained in the third odor information group has a negative value. The third odor information group wherein the odor information which has a negative value is excluded, may be defined as a fourth odor information group (1). The odor information contained in the fourth odor information group (1) does not contain odor information which has a negative value, but has only odor information with 0 (zero) or positive values.

(Adjustment Step S5-B)

The adjustment step S5-B is a step replacing a numerical value of the particular odor information with 0 (zero) when the particular odor information contained in the third odor information group has a negative value. The third odor information group wherein the numerical value of odor information which has a negative value is replaced with 0 (zero) can be defined as a fourth odor information group (2). The odor information contained in the fourth odor information group (1) does not contain odor information which has a negative value, but has only odor information with 0 (zero) or positive values.

(Adjustment Step S5-C)

The adjustment step S5-C is a step adding an absolute value of a particular odor information numerical value to every odor information which the third odor information group has when the particular odor information numerical value contained in the third odor information group has a negative value. When there is particular odor information which has negative numerical values, it is preferable to add an absolute value of the particular odor information numerical value having the largest absolute value of negative value. The third odor information group wherein the largest absolute value of a particular odor information numerical value is added to every odor information of the third odor information group having a particular odor information of negative value can be defined as a fourth odor information group (3). The odor information contained in the fourth odor information group (3) does not contain odor information which has a negative value, but has only odor information with 0 (zero) or positive values.

(Adjustment Step S5-D)

The adjustment step S5-D is a step repeatedly adding the first odor information group or the second odor information group to the third odor information group when particular odor information contained in the third odor information group has a negative value until the particular odor information becomes 0 (zero) or a positive value. That is, for each odor information numerical value of the third odor information group, each odor information numerical value of the first odor information group or the second odor information group is repeatedly added so that the particular odor information numerical value which has a negative value become 0 (zero) or a positive value. At this time, when the third odor information group is a calculation result (difference) when the second odor information group is subtracted from the first odor information group, it is the first odor information group that is added to the third odor information group. When the third odor information group is a calculation result (difference) when the first odor information group is subtracted from the second odor information group, it is the second odor information group that is added to the third odor information group. The third odor information group wherein the first odor information group or the second odor information group is repeatedly added to the third odor information group until the particular odor information numerical value that had a negative value becomes 0 (zero) or a positive value can be defined as a fourth odor information group (4). The odor information contained in the fourth odor information group (4) does not contain odor information which has a negative value, but has only odor information with 0 (zero) or positive values.

<Extraction Step S6>

In the extraction step S6, part or all of the plurality of the odor information groups 2 is extracted from the previously created odor information database D2 (S107). FIG. 6 shows an exemplary odor information database D2. As shown in FIG. 6, the odor information database D2 contains odor information 3 associated with a particular odor and stored as odor information group 2. The odor information database D2 contains a plurality of odor information groups 2. In FIG. 6, the difference values calculated for each sensor element 11 with respect to odor a and odor b are shown. For odor a, the difference value calculated using sensor element 11-01 is "38.7" and the difference value calculated using sensor element 11-02 is "27.0". The difference values (odor information) calculated by using these sensor elements are combined to obtain odor information group 2 for the odor a. In FIG. 6, for convenience, only the difference values (odor information) of sensor elements 11-01 to 11-07 are shown.

<Similarity Calculation Step S7>

In the similarity calculation step S7, a degree of similarity between the odor information group 2 extracted from the database D1 in extraction step S6 and the third odor information group or the fourth odor information group is calculated (S108). That is, each odor information 3 included in the odor information group 2 extracted from the odor information database D2 in extraction step S6 is compared with each odor information 3 included in the third odor information group or the fourth odor information group by the corresponding odor information 3, and a degree of similarity is calculated. The third odor information group is compared when no adjustments were made in adjustment step S5. It is to be noted that "odor information 3 corresponding to each other" means odor information 3 detected using the same sensor element.

The calculation of degree of similarity can be calculated as degree of similarity between vectors when odor information group 2 is regarded as a vector whose coordinate is odor information 3 included in odor information group 2. When the odor information group 2 contains n numerical values of odor information 3, the vector is a n-dimensional vector.

Specifically, the degree of similarity can be obtained by calculating various indices such as cosine similarity, cosine similarity (score value) for a value ($\theta/\pi$) obtained by dividing an angle $\theta$ formed by both vectors in cosine similarity by $\pi$, inter-vector distances, Pearson correlation coefficients, and deviation pattern similarity. As degree of similarity, score value, cosine similarity, Pearson correlation coefficient, deviation pattern similarity is higher in degree of similarity when the score value is closer to 1, and the inter-vector distance is higher in degree of similarity when the score value is smaller.

<Selection Step>

In the selection step, a specific odor information group 2 is selected from the plurality of odor information group 2 extracted from the database D1 in extraction step S6 based on degree of similarity calculated in similarity calculation step S7. For example, an odor information group 2 whose degree of similarity with the third odor information group or the fourth odor information group is higher than a predetermined threshold may be selected from a plurality of odor information groups 2 extracted from the database D1, or one or more odor information group 2 whose degree of similarity is the highest may be selected.

Embodiment 2

Figure 7:
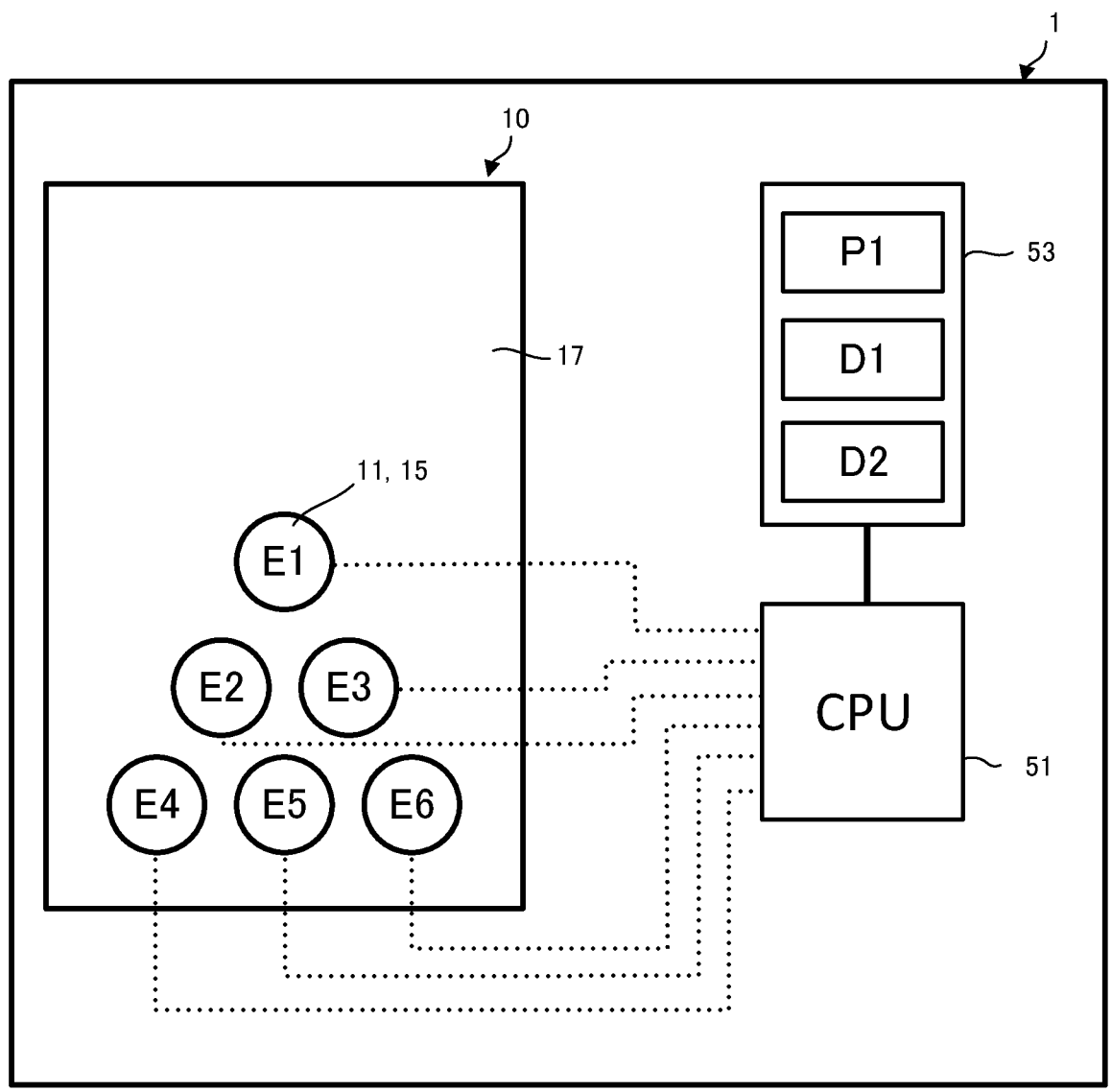
FIG. 7 is a schematic diagram showing an outline of the odor exploration system 1.

Next, an odor exploration system 1 according to Embodiment 2 will be described referring to Drawings. FIG. 7 is a schematic diagram showing an outline of the odor exploration system 1. The odor exploration system 1 has an odor sensor 10, a generator, a preparer, and a calculator. The generator generates odor information 3 which consists of numerical values by respectively quantifying each detection signal from a plurality of sensor elements, and generates a first odor information group consisting of odor information 3 generated based on detected result of a first gas. The preparer prepares a second odor information group consisting of odor information 3 generated on the basis of a detected result in which a second gas differing from the first gas is detected by a plurality of sensor elements. The calculator calculates a sum of or a difference between the second odor information group and the first odor information group based on the sum of or the difference between odor information 3 generated for the first gas and for the second gas using the same sensor element.

The odor exploration system 1 may further include an extractor extracting part or all of odor information group 2 from an odor information database D2 in which odor information group 2 including third odor information is stored, a similarity calculator calculating the degree of similarity between part or all of odor information group 2 from a plurality of odor information groups 2 extracted by the extractor and third odor information group, and a selector selecting specific odor information group 2 from a plurality of odor information groups 2 based on a degree of similarity calculated by the similarity calculator.

An arithmetic processing device 51 as an arithmetic unit can realize functions such as generating, preparing, calculating, extracting, similarity calculating, and selecting. The odor exploration system 1 can implement the odor exploration method described above.

<Odor Sensor 10>

Figure 8:
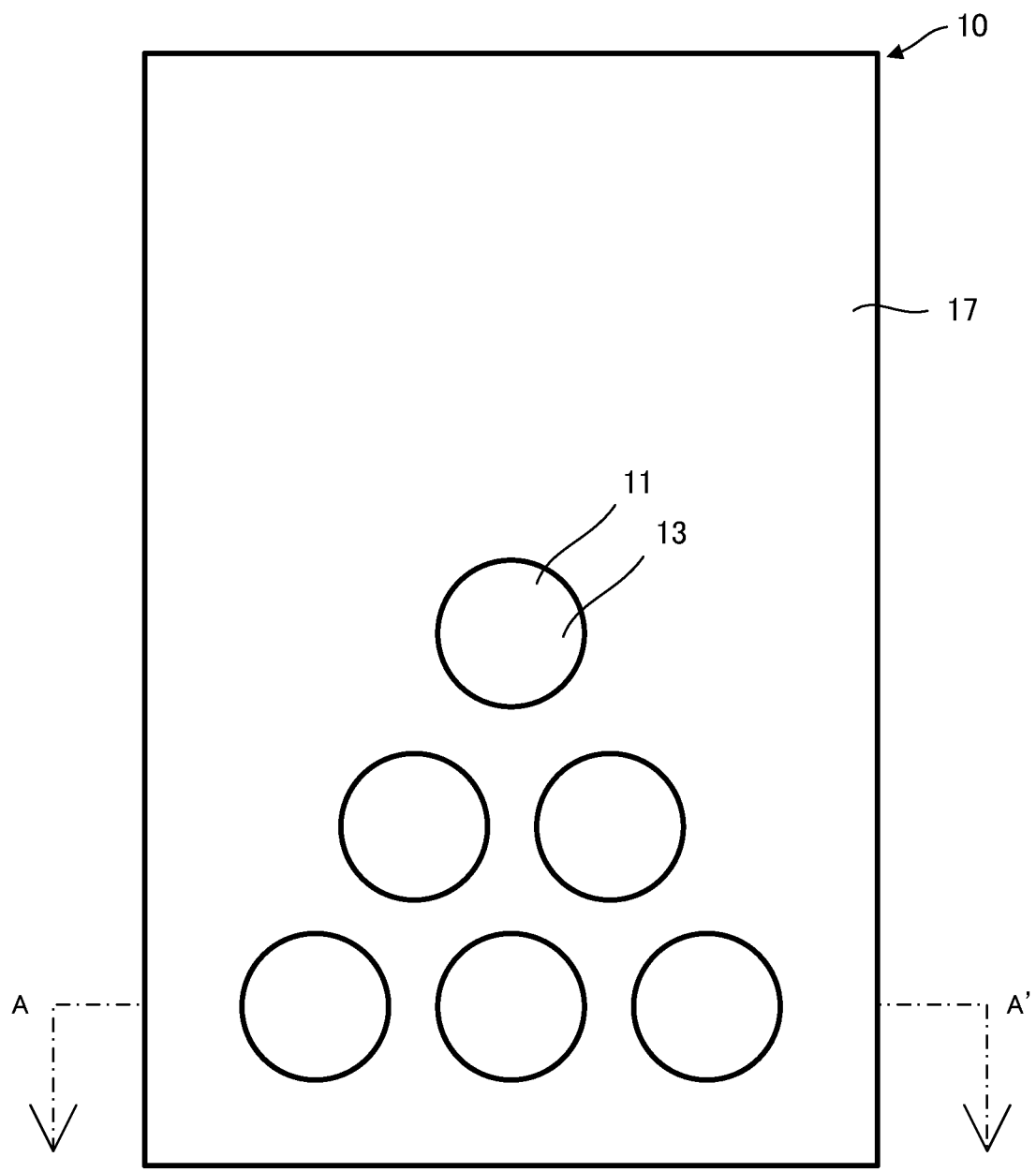
FIG. 8 is a plan view schematically illustrating the odor sensor 10.
Figure 9:
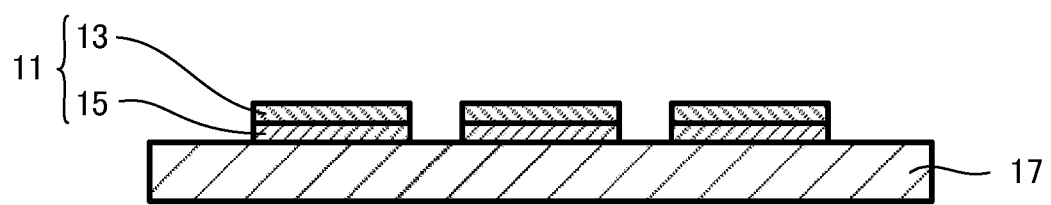
FIG. 9 is a cross-sectional view schematically illustrating the A-A' cross section of FIG. 8.

FIG. 8 is a plan view schematically illustrating the odor sensor 10. FIG. 9 is a cross-sectional view schematically illustrating the A-A' cross section of FIG. 8. The odor sensor 10 includes a plurality of sensor elements 11. Each of the sensor elements 11 includes the substance adsorbing membrane 13 that adsorbs the odor substance and a detector 15 that detects an adsorption state of the odor substance with respect to the substance adsorbing membrane 13.

As shown in FIGS. 8 and 9, the sensor element 11 includes the detector 15 and the substance adsorbing membrane 13 provided on the surface of the detector 15. It is preferable that the substance adsorbing membrane 13 covers the entire surface of the detector 15. That is, the size of the detector 15 is preferably the same as the formation range of the substance adsorbing membrane 13, or smaller than the formation range of the substance adsorbing membrane 13. Incidentally, a plurality of detectors 15 may be provided within the formation range of one substance adsorbing membrane 13.

A plurality of sensor elements 11 is disposed on a sensor substrate 17, and six sensor elements 11 as shown in FIG. 8 may be aligned so as to draw an equilateral triangle. In this instance, substance adsorbing membranes 13 of adjacent sensor elements 11 are not in contact with each other or are insulated. Incidentally, the sensor elements 11 may not be aligned on the sensor substrate 17 and may be randomly arranged or aligned in any form. Incidentally, it is not necessary that a sensor element 11 corresponding to all of odor information 3 for constituting the one odor information group 2 is provided on one sensor substrate 17, and different sensor elements 11 may be provided on a plurality of sensor substrates 17.

It is preferable that, in the plurality of sensor elements 11 arranged on the sensor substrate 17, properties of the respective substance adsorbing membranes 13 are different from each other. Specifically, it is preferable that all the plurality of sensor elements 11 have the substance adsorbing membranes 13 of different compositions, and that substance adsorbing membranes 13 of the same property do not exist. Here, the property of the substance adsorbing membrane 13 can be referred to as the adsorption characteristic of the odor substance with respect to the substance adsorbing membrane 13. That is, one same odor substance (or an aggregate thereof) can exhibit different adsorption characteristics if the substance adsorbing membrane 13 has different property. In FIG. 8 and FIG. 9, for the sake of convenience, all the substance adsorbing membranes 13 are illustrated in the same manner. However, in practice, properties thereof are different from each other. Incidentally, it is not necessary that the adsorption characteristics of all of the substance adsorbing membranes 13 of each of the sensor elements 11 are different from each other, and among them, the sensor elements 11 provided with the substance adsorbing membranes 13 having the same adsorption properties may be provided.

As a material of the substance adsorbing membrane 13, it is possible to use a thin film formed of a n-electron conjugated polymer. This thin film can contain at least one of an inorganic acid, an organic acid, or an ionic liquid as a dopant. By changing the type or content of the dopant, it is possible to change the property of the substance adsorbing membrane 13.

Examples of the n-electron conjugated polymer preferably include, but are not limited to, a polymer having the n-electron conjugated polymer as a skeleton such as polypyrrole and a derivative thereof, polyaniline and a derivative thereof, polythiophene and a derivative thereof, polyacetylene and a derivative thereof, or polyazulene and a derivative thereof.

In a case in which the n-electron conjugated polymer is in an oxidized state and the skeleton polymer itself is a cation, conductivity can be developed by containing an anion as a dopant. Incidentally, in the invention, a neutral n-electron conjugated polymer not containing a dopant can be adopted as the substance adsorbing membrane 13.

Specific examples of the dopant can include inorganic ions such as chlorine ion, chlorine oxide ion, bromine ion, sulfate ion, nitrate ion, and borate ion, organic acid anions such as alkylsulfonic acid, benzenesulfonic acid, and carboxylic acid, and polymer acid anions such as polyacrylic acid and polystyrene sulfonic acid.

In addition, it is possible to use a method of performing chemical equilibrium doping by allowing salt such as table salt or an ionic compound containing both a cation and an anion such as an ionic liquid to coexist with the neutral n-electron conjugated polymer.

In a case in which a state in which one dopant unit (ion) enters per two repeating units included in the n-electron conjugated polymer is set to 1, the content of the dopant in the n-electron conjugated polymer may be adjusted in a range of 0.01 to 5, preferably in a range of 0.1 to 2. When the content of the dopant is set to be greater than or equal to the minimum value of this range, it is possible to inhibit disappearance of the characteristic of the substance adsorbing membrane 13. In addition, when the content of the dopant is set to be less than or equal to the maximum value of this range, it is possible to inhibit a decrease in effect of the adsorption characteristic of the n-electron conjugated polymer itself, which makes it difficult to produce the substance adsorbing membrane 13 having a desirable adsorption characteristic. In addition, it is possible to inhibit a significant decrease in durability of the substance adsorbing membrane 13 due to the dopant, which is a low molecular weight substance, when predominant in the membrane. Therefore, by setting the content of the dopant in the above-mentioned range, it is possible to suitably maintain detection sensitivity of the odor substance.

In the plurality of sensor elements 11, different types of n-electron conjugated polymers can be used to vary the respective adsorption characteristics of the substance adsorbing membranes 13. In addition, respective adsorption characteristics may be developed by changing the type or the content of the dopant while using the same kind of n-electron conjugated polymer. For example, hydrophobic/hydrophilic properties of the substance adsorbing membrane 13 can be changed by changing the type of the n-electron conjugated polymer, the type and the content of the dopant, etc.

A thickness of the substance adsorbing membrane 13 can be appropriately selected according to the characteristic of the odor substance to be adsorbed. For example, the thickness of the substance adsorbing membrane 13 can be in a range of 10 nm to 10 μm, preferably 50 nm to 800 nm. When the thickness of the substance adsorbing membrane 13 is less than 10 nm, sufficient sensitivity may not be obtained in some cases. In addition, when the thickness of the substance adsorbing membrane 13 exceeds 10 m, an upper limit of the weight detectable by the detector 15 may be exceeded.

The detector 15 has a function as a signal converter (transducer) which measures a change in physical, chemical, or electrical characteristic of the substance adsorbing membrane 13 due to the odor substance adsorbed on the surface of the substance adsorbing membrane 13 and outputs measurement data thereof as, for example, an electric signal. That is, the detector 15 detects an adsorption state of the odor substance on the surface of the substance adsorbing membrane 13. Examples of the signal output as the measurement data by the detector 15 include physical information such as an electric signal, light emission, a change in electric resistance, or a change in vibration frequency.

The detector 15 is not particularly limited as long as the detector 15 is a sensor which measures the change in physical, chemical, or electrical characteristic of the substance adsorbing membrane 13, and various sensors can be appropriately used.

Specific examples of the detector 15 include a quartz oscillator sensor (QCM), a surface elastic wave sensor, a field effect transistor (FET) sensor, a charge coupled device sensor, an MOS field effect transistor sensor, a metal oxide semiconductor sensor, an organic conductive polymer sensor, an electrochemical sensor.

Incidentally, in the case of using the quartz oscillator sensor as the detector 15, although not illustrated, as an excitation electrode, electrodes may be provided on both sides of the crystal oscillator or a separated electrode may be provided on one side to detect a high Q value. In addition, the excitation electrode may be provided on the sensor substrate 17 side of the quartz oscillator with the sensor substrate 17 interposed therebetween. The excitation electrode can be formed of an arbitrary conductive material. Specific examples of the material of the excitation electrode include inorganic materials such as gold, silver, platinum, chromium, titanium, aluminum, nickel, nickel alloy, silicon, carbon, and carbon nanotube, and organic materials such as conductive polymers such as polypyrrole and polyaniline.

As illustrated in FIG. 8 and FIG. 9, the detector 15 can have a flat-plate shape. As illustrated in FIG. 8, a shape of the flat plate of the flat-plate shape can be can be circular, but can also be of various shapes such as quadrilateral, square, elliptical, etc. However, the shape can be of various shapes such as a circle or an ellipse. Further, the shape of the detector 15 is not limited to the flat plate shape. A thickness thereof may be altered, and a concave portion or a convex portion may be formed.

In a case in which the detector 15 uses an oscillator as the quartz oscillator sensor described above, it is possible to reduce the influence (crosstalk) received from another oscillator coexisting on the same sensor substrate 17 by changing resonance frequencies of respective oscillators in the plurality of sensor elements 11. It is possible to arbitrarily design the resonance frequencies so that the respective oscillators on the same sensor substrate 17 exhibit different sensitivities with respect to a certain frequency. The resonance frequency can be changed, for example, by adjusting the thickness of the oscillator or the substance adsorbing membrane 13.

As the sensor substrate 17, it is possible to use a silicon substrate, a substrate made of quartz crystal, a printed wiring substrate, a ceramic substrate, a resin substrate, etc. In addition, the substrate is a multilayer wiring substrate such as an interposer substrate, and an excitation electrode for oscillating the quartz substrate, mounting wirings, and an electrode for energizing are disposed at arbitrary positions.

By adopting the configuration as described above, it is possible to obtain the odor sensor 10 including the plurality of sensor elements 11 having the substance adsorbing membranes 13 whose adsorption characteristics of the odor substance are different from each other. As a result, in a case in which an odor of air containing a certain odor substance or a composition thereof is measured by the odor sensor 10, the odor substance or the composition thereof comes into contact with the substance adsorbing membrane 13 of each sensor element 11 in the same manner. However, the odor substance is adsorbed to the respective substance adsorbing membranes 13 in different modes. That is, an adsorption amount of the odor substance is different between the respective substance adsorbing membranes 13. For this reason, a detection result of the detector 15 is different between the respective sensor elements 11. Therefore, pieces of measurement data by the detector 15 corresponding to the number of sensor elements 11 (substance adsorbing membranes 13) included in the odor sensor 10 are generated for the certain odor substance or the composition thereof.

A set of measurement data generated by the odor sensor 10 by measuring the certain odor substance or the composition thereof is usually specific (unique) to a specific odor substance or a composition of the odor substance. For this reason, by measuring data using the odor sensor 10, it is possible to identify the odor as an odor substance alone or as a composition (mixture) of odor substances.

<Arithmetic Unit>

The generator, the preparer, and the calculator of the odor exploration system 1 can be realized by an arithmetic processing device 51 as an arithmetic unit. As shown in FIG. 7, the arithmetic processing device 51 is communicatively connected to each of the sensor elements 11 of the odor sensor 10 and can read detected result detected by each of the sensor elements 11 by the arithmetic processing device 51 and calculate based on it. The arithmetic processing device 51 may be connected to a storage device 53. The storage device 53 can store a program P1 which realizes e.g., the generator, the preparer, and the calculator. In addition, the storage device 53 can store detection signal database D1 and odor information database D2.

EXAMPLES

Example 1

It is known that the odor of lemon, the odor of lime, and the odor of cinnamon give the odor of cola when they are combined. Based on such finding, this was verified using the odor exploration system 1 of Embodiment 2.

(Sensory Test)

Sensory tests were carried out using odor samples of lemon, lime, and cinnamon provided by Aromaster. Approximately 10 µl of each odor sample was dropped onto perfume test papers, respectively, and each perfume test paper was enclosed in sample bottles. After 10 minutes of standing, the sample bottles were opened and subjected to a sensory test by human testers. As a result of the sensory test, 7 out of 7 persons were evaluated as having an odor close to cola.

Example 1-1

An odor sample of lemon and an odor sample of cinnamon provided by Aromaster were premixed, and a first odor information group containing a difference value of detection signal was generated for the mixed odor sample. A second odor information group containing difference values of detection signal was generated regarding an odor sample of lime provided by Aromaster. The sum of the first odor information group and the second odor information group was calculated to generate the third odor information group.

The degree of similarity between the plurality of odor information groups extracted from the odor information database D2 and the third odor information group was calculated, and the extracted plurality of odor information groups were sorted in descending order by the degree of similarity, and the top 3 odor information groups were selected. The degree of similarity was calculated using cosine similarity and sorted based on this. The various requirements of Example 1-1 are shown in diagram 1000 of FIG. 10. The selection results of Example 1-1 are shown in diagram 1100 of FIG. 11. In the odor information database D2, the odor information group generated by using odor sensor 10 for odors of various samples is stored in association with labels of the samples. A detailed description of each sample used in the Examples is given in Table 1.

The measurement method of each sample was carried out depending on its state. When the condition of the sample was liquid, 10 mL of sample was poured into a vial bottle having a volume of 20 mL, and measurement was performed by bringing the opening of the vial bottle close to the odor sensor 10. When the samples were aroma oil, they were measured by bringing the opening of the aroma oil container close to the odor sensor 10. When the state of the sample was liquid, a sample obtained by dropping a few drops of the sample onto a mueth (perfume paper) was placed in a sample bottle, and measurement was performed by bringing the opening of the sample bottle close to odor sensor 10. When the sample was solid, the sample was placed in a vial bottle of 20 mL and measurement was performed by bringing the opening of the vial bottle close to the odor sensor 10. When the sample cannot be contained in a vial bottle with a volume of 20 mL, it was crushed and pulverized to such an extent that it can enter the vial bottle as appropriate. When the condition of the sample was gaseous, a cloth exposed to the sample was placed in a sample bottle and measurement was performed by bringing the opening of the sample bottle close to the odor sensor 10. When the sample was a smoker's breath, a fabric was exposed to the sample by blowing the smoker's breath during smoking onto the fabric.

For the odor measurements, an odor measurement apparatus having an odor sensor 10 inside and an introduction port for introducing external air onto the odor sensor 10 was used. The odor of the samples was measured by bringing the opening of the vial bottles or sample bottles close to about 1 cm in the vicinity of the introduction port and holding the vial bottles or sample bottles at that position for about 5 seconds.

TABLE 3

| Label | Item | Condition | Remarks |
|---|---|---|---|
| Alcohol drink A | Shochu high ball Lemon (Takara) | Liquid | |
| Alcohol drink B | Shochu "Kana" (Alcohol content: 40%) (Nishihira Shuzo) | Liquid | |
| Alcohol drink C | Shochu "Nagakumo Ichibanbashi" (Alcohol content: 30%) (Yamada Shuzo) | Liquid | |
| Alcohol drink D | "Horoyoi Lemon" (Registered Trademark) (Suntory Beverage & Food Limited) | Liquid | |
| Alcohol drink E | Japanese Sake (Kamaya) | Liquid | |
| Alcohol drink F | Japanese Sake "Senchu Hassaku" (Tsukasa Botan) | Liquid | |
| Aroma oil A | Essential oil Orange Sweet (Organic) (Natural Organic) | Liquid | |
| Aroma oil B | Essentail oil Ylang ylang (Tree of Life Co., Ltd.) | Liquid | |
| Aroma oil C | Wine Aroma kit (88 Aromas) Guava (Aromaster) | Liquid | |
| Aroma oil D | Wine Aroma kit (88 Aromas) Tomato (Aromaster) | Liquid | |
| Aroma oil E | Wine Aroma kit (88 Aromas) Lemon (Aromaster) | Liquid | |
| Fruit juice drink A | Apple juice (Dole) | Liquid | |
| Machine oil | Machine oil | Liquid | |
| Smoker's breath A | Breath when smoking tobacco (Mild Seven) | Gaseous | Measurement performed for a fabric exposed to by blowing the tester's breath |
| Fregrance A | Fregrance Green Lemon (Whitte) | Liquid | |
| Synthetic sample A | Aroma oil (Aromaster) Black tea + Lemon | Liquid | Measurement performed for two mueths placed in a sample bottle onto which aroma oils of black tea and lemon were respectively poured |
| Synthetic sample B | Aroma oil (Aromaster) Lemon + Cinnamon | Liquid | Measurement performed for two mueths placed in a sample bottle onto which aroma oils of lemon and cinnamon were respectively poured |
| Black tea A | Earl Grey tea leaf (Janat) | Solid | |
| Black tea B | Earl Grey tea leaf (TWINING) | Solid | |
| Black tea C | Rose Red tea leaf (Tree of Life Co., Ltd.) | Solid | |
| Coffee drink A | Aroma Blend HC (Hisamitsu Coffee) | Liquid | |
| Coffee drink B | Brazil Tomio Fukuda Dried on tree | Liquid | Coffee extracted from coffee beans Brazil Tomio Fukuda Dried on tree |
| Coffee drink C | Tanzania Ngoro AA Heights Farm | Liquid | Coffee extracted from coffee beans Tanzania Ngoro AA Heights Farm |
| Coffee drink D | Dark Blend (Hisamitsu Coffee) | Liquid | |
| Cola drink A | Pepsi (Registered trademark) Cola (Suntory Beverage & Food Limited) | Liquid | |
| Cola drink B | Coca Cola (Registered trademark) (Coca-Cola (Japan)) | Liquid | |
| Reagent A | Vanillin (FUJIFILM Wako Pure Chemical Corporation) | Solid | Measurement performed for vanillin in powder placed in at more than half of a 5 mL sample bottle |
| Reagent B | ultrapure water (FUJIFILM Wako Pure Chemical Corporation) | Liquid | |
| Reagent C | Ammonia water (Japanese Pharmacopoeia) | Liquid | Adusted to concentration of 3% with water |
| Reagent D | Anhydriys ethanol (Kenei Pharmaceutical Co., Ltd.) | Liquid | |
| Reagent E | Acetone (FUJIFILM Wako Pure Chemical Liquid Corporation) | | |
| Shower gel | Shower gel LUSH Bergamot (LUSH) | Liquid | |
| Shampoo A | "Ichikami" (Registered trademark) "Jun wasoyu" (Kracie) | Liquid | |
| Hair dressing A | Pomade (Ynagiya) | Solid | Product of Yanagiya |
| Essentail oil A | Wa Essentail oil (mint) (Tree of Life Co., Ltd.) | Liquid | |
| Chocolate A | Dars milk (Morinaga & Co.) | Solid | |
| Chocolate B | EXCELLENCE Cacao 90% (LINDT & SPRUNGLI JAPAN) | Solid | |

TABLE 3-continued

| Label | Item | Condition | Remarks |
|---|---|---|---|
| Bedbug | Bedbug | Solid | Measurement performed for air in an airbag into which three bedbugs are placed |
| Framboise | Fruit juice of framboise | Solid | Measurement performed for crushed fresh framboise placed in a sample bottle |
| Body milk A | Biore Prime body oil oil in body milk (Kao Corporation) | Liquid | |
| Lemon drink A | Apple juice (Dole) + "Chelate Lemon" (Registered trademark) (POKKA SAPPORO FOOD & BEVERAGE LTD.) | Liquid | Measurement performed for 5 mL each of apple juice and Chelate Lemon mixed and the sum up of 10 mL placed in a 20 mL vial bottle |

As shown in FIG. 11, in Example 1-1, the odor information group having the highest degree of similarity with the third odor information group (highest degree of similarity) was the odor information group generated for Cola Drink A (Pepsi® Cola manufactured by Suntory Food International Co., Ltd.). The odor information group of second highest degree of similarity was the odor information group generated for black tea A (using Earl Gray tea leaves manufactured by Janat) and the odor information group of third highest degree of similarity was the odor information group generated for aroma oil D (using "tomato" aroma oil from among the Aromaster wine aroma kits (88 aromas)).

Examples 1-2 to 1-10

The odor information group was selected in the same manner as in Example 1-1, except that the condition shown in FIG. 10 was used. For Examples 1-4 to 1-10, when the odor information contained in the third odor information group has a negative value, a fourth odor information group was generated excluding odor information which had negative value, and the degree of similarity was calculated based on the fourth odor information group. The selection results for Examples 1-2 to 1-10 are shown in FIG. 11.

Example 2

It is known that the odor of isovaleric acid combined with the odor of vanillin gives the odor of chocolate. Based on such finding, this was verified using odor exploration system 1 of Embodiment 2.

(Sensory Test)

Sensory tests were carried out using a 1000-fold diluted aqueous solution of isovaleric acid and an odor sample of vanillin manufactured by Aromaster. A cotton swab onto which a 1000-fold diluted aqueous solution of isovaleric acid was added in trace drops and a cotton swab onto which about 10 mg of an odor sample of vanillin was added dropwise were enclosed in a sample bottle. After 10 minutes of standing, the sample bottles were opened and subjected to a sensory test by human testers. As a result of the sensory test, 9 out of 9 persons have evaluated as having a scent close to chocolate.

Examples 2-1, 3-1 to 3-3

The odor information group was selected in the same manner as in Example 1-1, except that the condition shown in diagram 1200 of FIG. 12 was used. For Examples 3-1 to 3-3, when the odor information contained in the third odor information group has a negative value, a fourth odor information group was generated excluding odor information which had negative value, and the degree of similarity was calculated based on the fourth odor information group. The selection results of Examples 2-1, 3-1 to 3-3 are shown in diagram 1300 of FIG. 13. A detailed description of each sample used in the Examples is given in Table 1.

As described above, preferred embodiment of the present invention has been described, but the present invention is not limited thereto, and various modifications and changes can be performed within the scope of the point of the present invention. For example, the present invention includes the following points.

(Point 1) An odor exploration method exploring odor based on odor information generated by
    (1) a plurality of sensor elements each outputting a detection signal according to the state of adsorption by indicating an adsorption reaction unique to each odor substance, and
    (2) an arithmetic unit generating the odor information which consists of numerical values, by quantifying each detection signal outputted from the plurality of sensor elements;
  wherein the odor exploration method including:
  a detection step detecting a first gas containing a plurality of odor substances with the plurality of sensor elements;
  a generation step generating a first odor information group consisting of the odor information generated based on a detection result of the first gas;
  a preparation step preparing a second odor information group consisting of odor information generated based on a detection of a second gas different from the first gas with the plurality of sensor elements; and
  a calculation step calculating a sum of or a difference between the second odor information group and the first odor information group based on a sum of or difference between the odor information generated for the first gas and for the second gas using the same sensor element.

According to this, it is possible to provide an odor exploration method and an odor exploration system for exploring the odor obtained when different odors are mixed with each other, or the odor to be mixed with a specific odor in order to obtain a desired odor.

(Point 2) The odor exploration method may further include an adjustment step adjusting wherein, when a particular odor information numerical value in the odor information contained in a third odor information group has a negative value, the third odor information being a result of the difference between the second odor information group and the first odor information group, the particular odor information numerical value is excluded from the third odor information group.

(Point 3) The odor exploration method may further include an adjustment step adjusting wherein, when a particular odor information numerical value in the odor information contained in a third odor information group has a negative value, the third odor information being a result of the difference between the second odor information group and the first odor information group, the particular odor information numerical value is replaced with 0.

(Point 4) The odor exploration method may further include an adjustment step adjusting wherein, when a particular odor information numerical value in the odor information contained in a third odor information group has a negative value, the third odor information being a result of the difference between the second odor information group and the first odor information group, an absolute value of the particular odor information numerical value is added to every odor information numerical value which the third odor information group contains.

(Point 5) The odor exploration method may further include an adjustment step adjusting wherein, when a particular odor information numerical value in the odor information contained in a third odor information group has a negative value, the third odor information being a result of the difference between the second odor information group and the first odor information group, the second odor information group is repeatedly added to the third odor information group until the particular odor information numerical value become 0 or a positive value.

(Point 6) The odor exploration method may further include:
an extraction step extracting part or all of a plurality of odor information groups from a database in which the plurality of odor information groups are contained,
a similarity calculation step calculating a degree of similarity between the odor information groups which is part or all of the plurality of odor information groups extracted by the extraction step and the third odor information group, and
a selection step selecting a particular odor information group from the plurality of odor information groups based on the degree of similarity calculated in the similarity calculation step.

(Point 7) The odor exploration method may calculate the degree of similarity in the similarity calculation step includes calculating any one of cosine similarity, cosine similarity for a value (θ/n) obtained by dividing an angle θ formed by both vectors in cosine similarity by n, inter-vector distances, Pearson correlation coefficients, and deviation pattern similarity, when an odor information group is regarded as a vector whose coordinate is respectively an odor information included in the odor information group.

(Point 8) In the selection step of the odor exploration method, an odor information group having a higher degree of similarity than a predetermined threshold or an odor information group having the highest degree of similarity is selected as the particular odor information group.

(Point 9) An odor exploration system comprising:
an odor sensor having a plurality of sensor elements each outputting a detection signal according to the state of adsorption by indicating an adsorption reaction unique to each odor substance, and detecting a first gas containing a plurality of odor substances with the plurality of sensor elements;
a generator generating odor information which consists of numerical values by quantifying each detection signal from the plurality of sensor elements, and generating a first odor information group consisting of the odor information generated based on a detection result of the first gas;
a preparer preparing a second odor information group consisting of odor information generated based on a detection of a second gas different from the first gas with the plurality of sensor elements; and
a calculator calculating a sum of or a difference between the second odor information group and the first odor information group based on a sum of or difference between the odor information generated for the first gas and for the second gas using the same sensor element.

REFERENCE SIGNS LIST

1: odor exploration system
2: odor information group
3: odor information
10: odor sensor
11: sensor element
13: substance adsorbing membrane
15: detector
17: sensor substrate
51: arithmetic processing device
53: storage device
D1: detection signal database
D2: odor information database

What is claimed is:

1. An odor exploration method exploring odor based on odor information, the method comprising:
for (1) a plurality of sensor elements each outputting a detection signal according to the state of adsorption by indicating an adsorption reaction unique to each odor substance, and
(2) an arithmetic unit:
a detection step detecting a first gas containing a plurality of odor substances with the plurality of sensor elements;
a generation step generating, by the arithmetic unit, a first group of odor information values by quantifying each detection signal outputted from the plurality of sensor elements for the first gas;
a preparation step preparing a second group of odor information values, the second group consisting of odor information generated by the arithmetic unit and based on of the plurality of sensor elements detecting a second gas different from the first gas; and
a calculation step calculating a sum of, or a difference between, the second group and the first group based on a sum of, or difference between, the odor information generated for the first gas and for the second gas using the same sensor element.

2. The odor exploration method according to claim 1, further comprising an adjustment step adjusting wherein, when a particular odor information numerical value in the odor information contained in a third group of odor information values has a negative value, the third group being a result of the difference between the second group and the first group, the particular odor information numerical value is excluded from the third group.

3. The odor exploration method according to claim 1, further comprising an adjustment step adjusting wherein, when a particular odor information numerical value in the odor information contained in a third group of odor information values has a negative value, the third group being a result of the difference between the second group and the first group, the particular odor information numerical value is replaced with 0.

4. The odor exploration method according to claim 1, further comprising an adjustment step adjusting wherein, when a particular odor information numerical value in the odor information contained in a third group of odor information values has a negative value, the third group being a result of the difference between the second group and the first group, an absolute value of the particular odor information numerical value is added to every odor information numerical value which the third group contains.

5. The odor exploration method according to claim 1, further comprising an adjustment step adjusting wherein, when a particular odor information numerical value in the odor information contained in a third group of odor information values has a negative value, the third group being a result of the difference between the second group and the first group, the second group is repeatedly added to the third group until the particular odor information numerical value become 0 or a positive value.

6. The odor exploration method according to claim 1, further comprising:
   an extraction step extracting part or all of a plurality of groups of odor information values from a database in which the plurality of groups are contained,
   a similarity calculation step calculating a degree of similarity between the groups of odor information values which is part or all of the plurality of groups of odor information values extracted by the extraction step and the third group, and
   a selection step selecting a particular group of odor information values from the plurality of groups of odor information values based on the degree of similarity calculated in the similarity calculation step.

7. The odor exploration method according to claim 6, wherein calculating the degree of similarity in the similarity calculation step further comprises:
   calculating any one of: a cosine similarity, a cosine similarity for a value ($\theta/\pi$) obtained by dividing an angle $\theta$ formed by both vectors in cosine similarity by $\pi$, inter-vector distances, Pearson correlation coefficients, and deviation pattern similarity,
   wherein a group of odor information values in the plurality of groups of odor information values comprises a vectors having coordinates.

8. The odor exploring method according to claim 6, wherein, in the selection step, a group of odor information values having a higher degree of similarity than a predetermined threshold or a group of odor information values having the highest degree of similarity is selected as the particular group of odor information values.

9. The odor exploring method according to claim 7, wherein, in the selection step, a group of odor information values having a higher degree of similarity than a predetermined threshold or a group of odor information values having the highest degree of similarity is selected as the particular group of odor information values.

10. An odor exploration system comprising:
    an odor sensor comprising a plurality of sensor elements, wherein each sensor element in the plurality of sensor elements outputs a detection signal according to the state of adsorption by indicating an adsorption reaction unique to each odor substance, and wherein the plurality of sensor elements detects a first gas containing a plurality of odor substances;
    a generator generating numerical odor information values by quantifying each detection signal from the plurality of sensor elements, and generating a first group of odor information values based on a detection result of the first gas;
    a preparer preparing a second group of odor information values generated based on the plurality of sensor elements detecting a second gas different from the first gas; and
    a calculator calculating a sum of, or a difference between, the second group and the first group based on a sum of, or difference between, values generated for the first gas and for the second gas using the same sensor element in the plurality of sensor elements.

11. The odor exploration method according to claim 1, wherein the first gas and the second gas are detected sequentially.

12. The odor exploration system according to claim 10, further comprising:
    an extractor extracting odor data from a database.

* * * * *